(12) United States Patent
Faizer et al.

(10) Patent No.: US 11,883,273 B2
(45) Date of Patent: Jan. 30, 2024

(54) COMPLIANT AORTIC STENT GRAFTS AND RELATED SYSTEMS AND METHODS

(71) Applicant: Regents of the University of Minnesota, Minneapolis, MN (US)

(72) Inventors: Rumi Faizer, Little Canada, MN (US); Victor Barocas, St. Paul, MN (US); Filippo Coletti, Minneapolis, MN (US); Shannen B. Kizilski, Minneapolis, MN (US); Ankurita Datta, Ithaca, NY (US); Omid Amili, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/609,148

(22) PCT Filed: Apr. 27, 2018

(86) PCT No.: PCT/US2018/029820
§ 371 (c)(1),
(2) Date: Oct. 28, 2019

(87) PCT Pub. No.: WO2018/200972
PCT Pub. Date: Nov. 1, 2018

(65) Prior Publication Data
US 2020/0188084 A1   Jun. 18, 2020

Related U.S. Application Data

(60) Provisional application No. 62/491,546, filed on Apr. 28, 2017.

(51) Int. Cl.
*A61F 2/07* (2013.01)
*A61F 2/848* (2013.01)
(Continued)

(52) U.S. Cl.
CPC .......... *A61F 2/07* (2013.01); *A61F 2002/068* (2013.01); *A61F 2002/077* (2013.01);
(Continued)

(58) Field of Classification Search
CPC .. A61F 2/04; A61F 13/2071; A61F 2002/068; A61F 2002/821;
(Continued)

(56) References Cited

U.S. PATENT DOCUMENTS 5,156,620 A * 10/1992 Pigott ............... A61M 25/1002
623/1.25
6,312,462 B1 * 11/2001 McDermott .............. A61F 2/07
623/1.25
(Continued)

FOREIGN PATENT DOCUMENTS

WO   WO 2015/183489   12/2015

OTHER PUBLICATIONS

International Search Report, Application No. PCT/US2018/029820, dated Jul. 10, 2018, 1 page.
(Continued)

*Primary Examiner* — Ann Schillinger
(74) *Attorney, Agent, or Firm* — Merchant & Gould, P.C.

(57) ABSTRACT

A vascular implant for an endoluminal stent or blood vessel, the stent or blood vessel defining a lumen for the passage of blood. The liner can comprise a flexible bladder arrangeable within the lumen, which can be fillable with a compressible fluid. The liner can define an inner lumen for the passage of blood. The liner and the fluid are conformable in response to a pulsatile pressure wave of the blood in the blood vessel such that the pressure within the blood vessel is reduced.

18 Claims, 15 Drawing Sheets

(51) Int. Cl.
*A61F 2/82* (2013.01)
*A61F 2/06* (2013.01)

(52) U.S. Cl.
CPC ............ *A61F 2230/0065* (2013.01); *A61F 2250/0003* (2013.01); *A61F 2250/0013* (2013.01)

(58) Field of Classification Search
CPC ...... A61F 2210/0014; A61F 2250/0003; A61F 2250/0006; A61F 2/07; A61F 2002/077; A61F 2230/0065; A61F 2250/0013
See application file for complete search history.

(56) References Cited

U.S. PATENT DOCUMENTS

| | | | |
|---|---|---|---|
| 6,926,743 | B1 | 8/2005 | Chuter |
| 7,762,980 | B2 | 7/2010 | Gertner |
| 8,118,856 | B2 | 2/2012 | Schreck |
| 8,821,564 | B2 | 9/2014 | Schreck |
| 9,579,187 | B1 | 2/2017 | Zukowski |
| 10,617,538 | B2 * | 4/2020 | Scandurra ........ A61B 17/12036 |
| 10,869,748 | B2 * | 12/2020 | Rosenberg .......... A61B 5/6862 |
| 2001/0023369 | A1 * | 9/2001 | Chobotov ................ A61F 2/06 623/1.11 |
| 2004/0193122 | A1 * | 9/2004 | Cline .................... A61F 5/448 604/332 |
| 2005/0171593 | A1 * | 8/2005 | Whirley .................. A61F 2/07 623/1.42 |
| 2007/0038292 | A1 * | 2/2007 | Danielpour .............. A61F 2/82 623/1.42 |
| 2008/0188923 | A1 * | 8/2008 | Chu ................ A61B 17/12136 623/1.15 |
| 2009/0138067 | A1 | 5/2009 | Pinchuk |
| 2011/0015475 | A1 * | 1/2011 | Hanuka .................... A61F 2/04 600/32 |
| 2012/0059387 | A1 * | 3/2012 | Schanz .................. A61F 2/958 606/108 |
| 2013/0079871 | A1 * | 3/2013 | Scandurra ................ A61F 2/82 623/1.36 |
| 2013/0079890 | A1 * | 3/2013 | Rousseau ............... A61B 17/11 623/23.68 |
| 2015/0374483 | A1 * | 12/2015 | Janardhan .......... B23K 26/1435 606/200 |

OTHER PUBLICATIONS

Takehisa Matsuda et al., *Development of Hybrid Compliant Graft: Rapid Preparative Method for Reconstruction of a Vascular Wall*, vol. XXXV, Trans Am Soc Artif Intern Organs, 1989, 3pages.

* cited by examiner

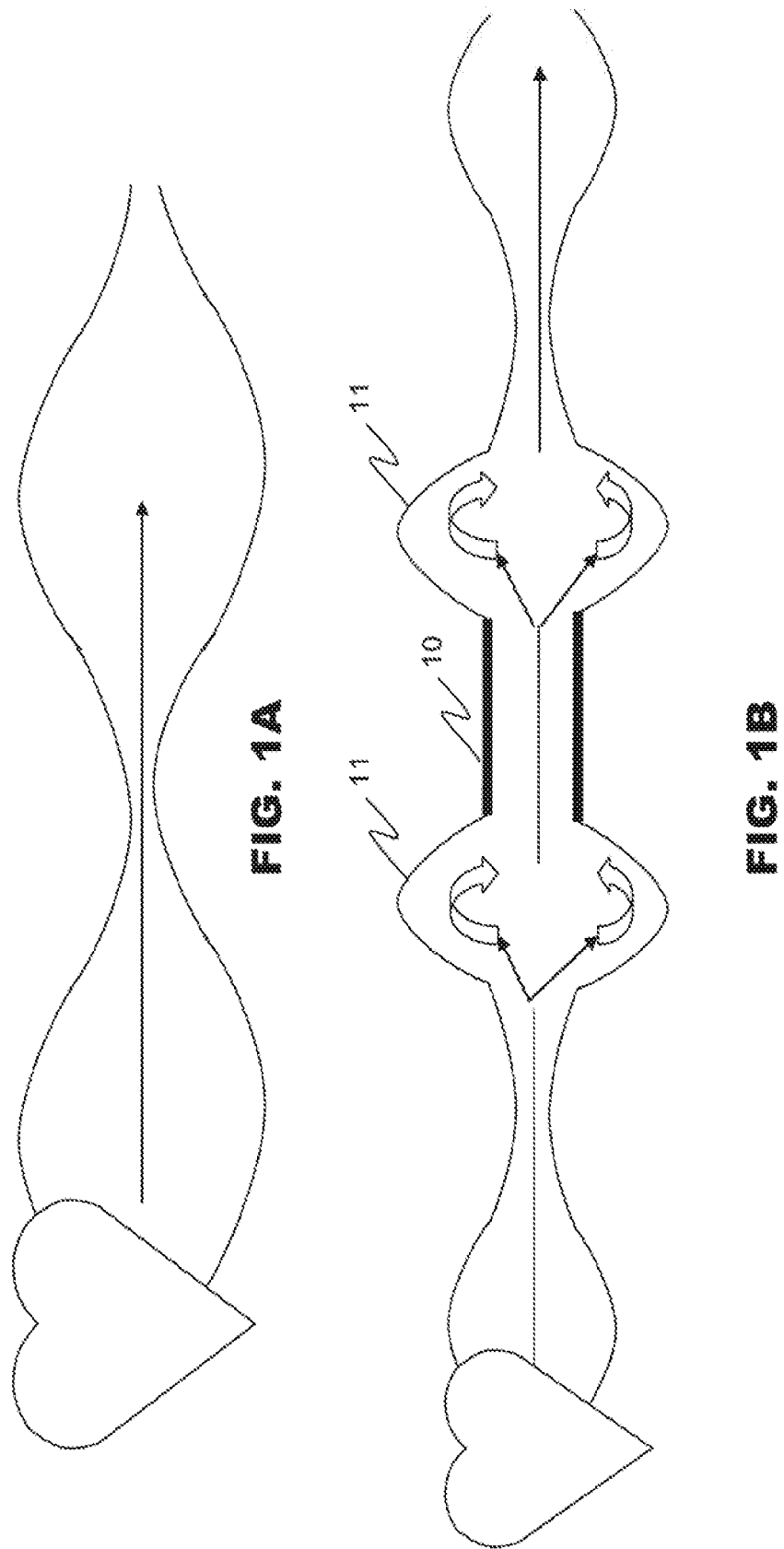

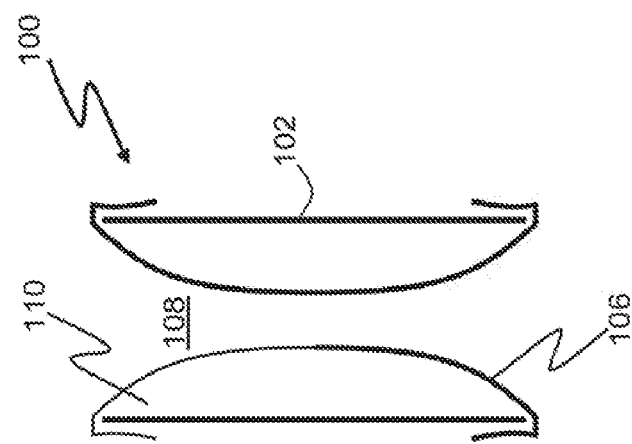
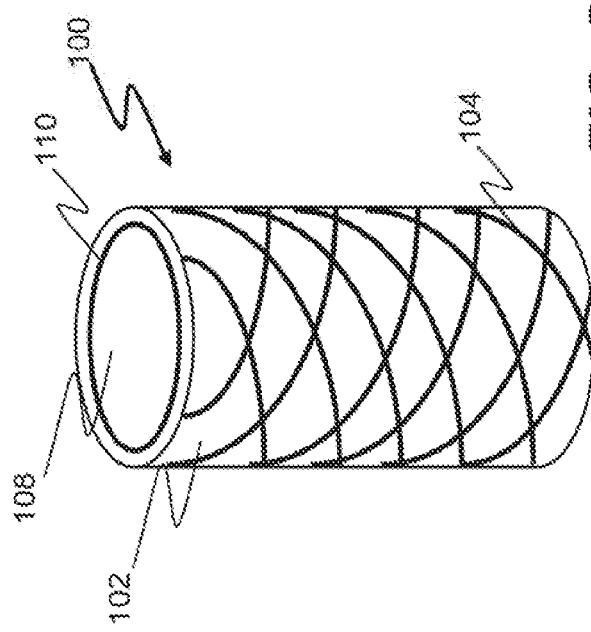
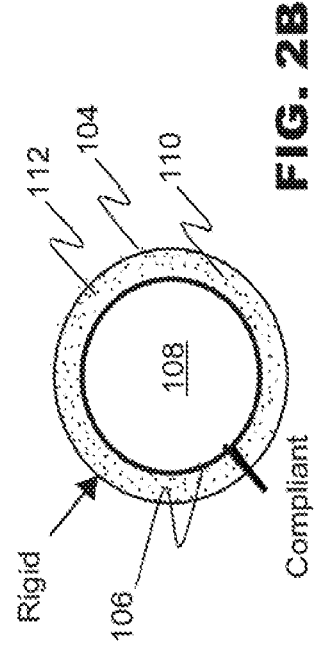
FIG. 2A
FIG. 2B
FIG. 2C

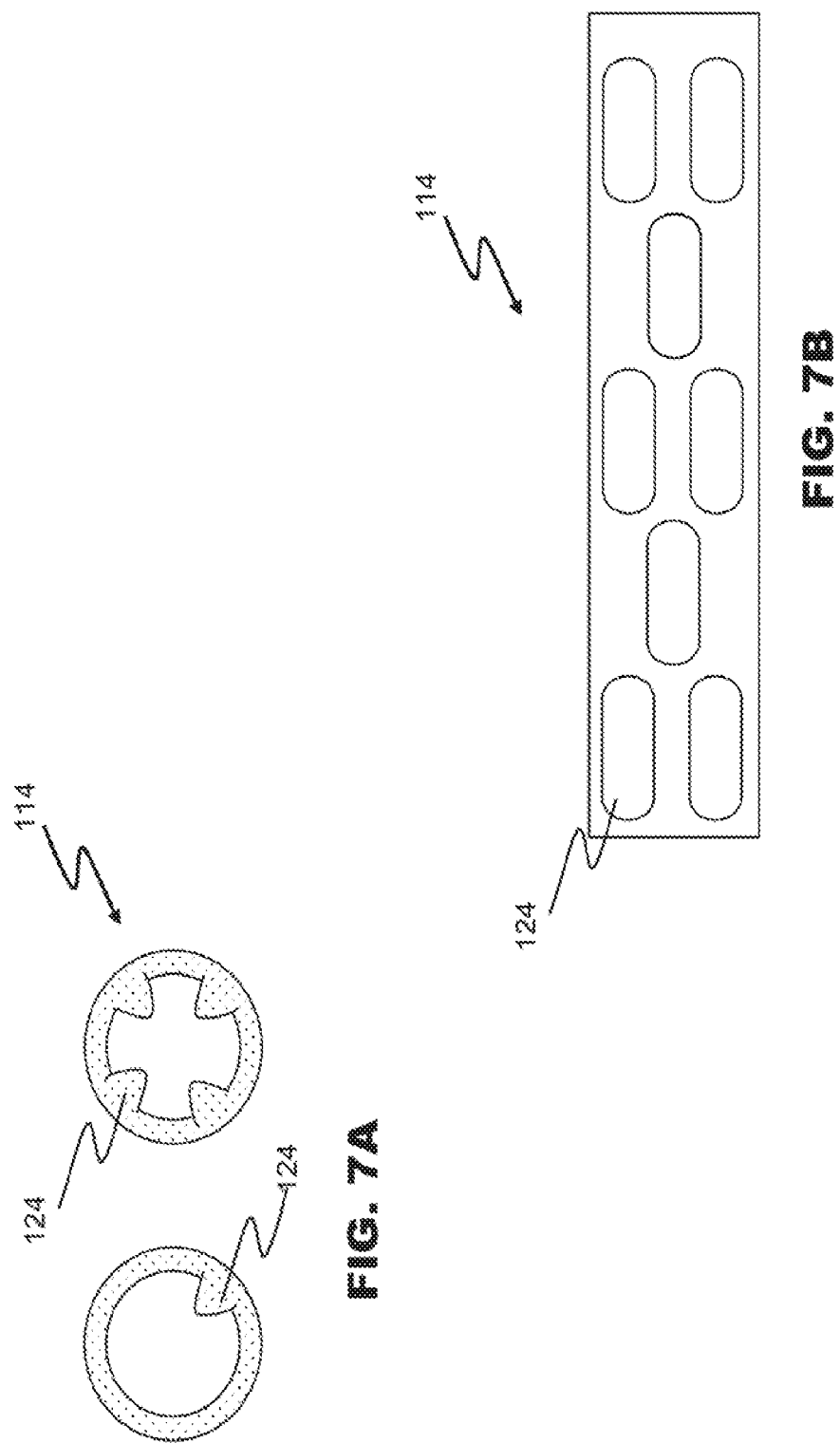

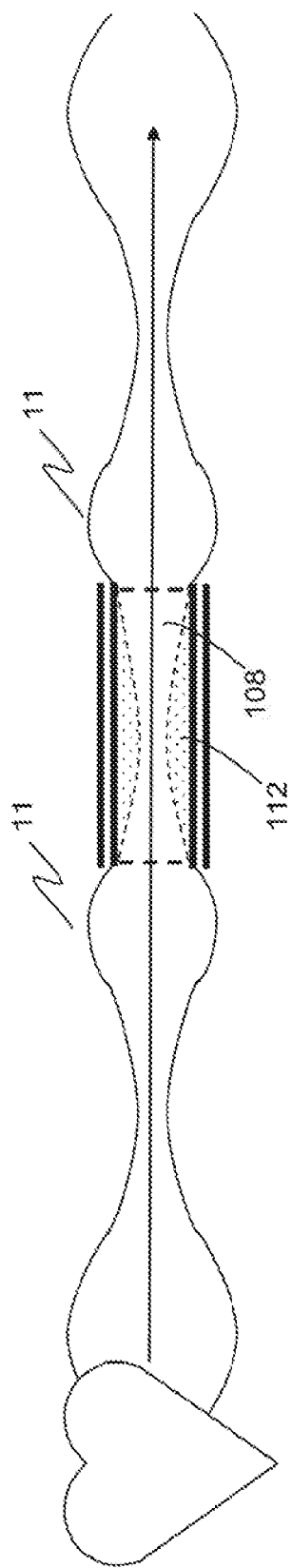

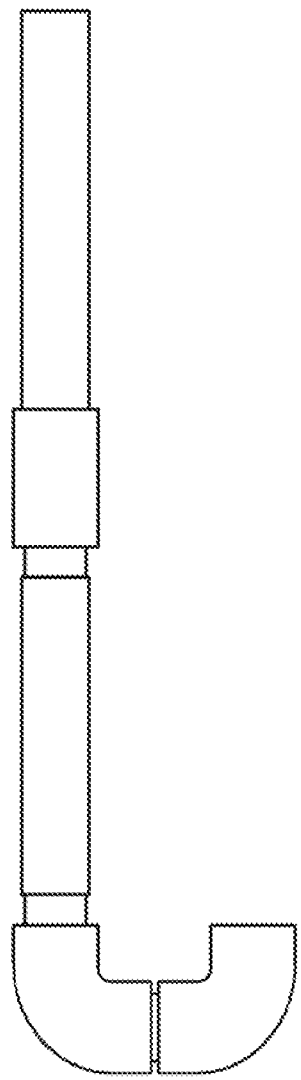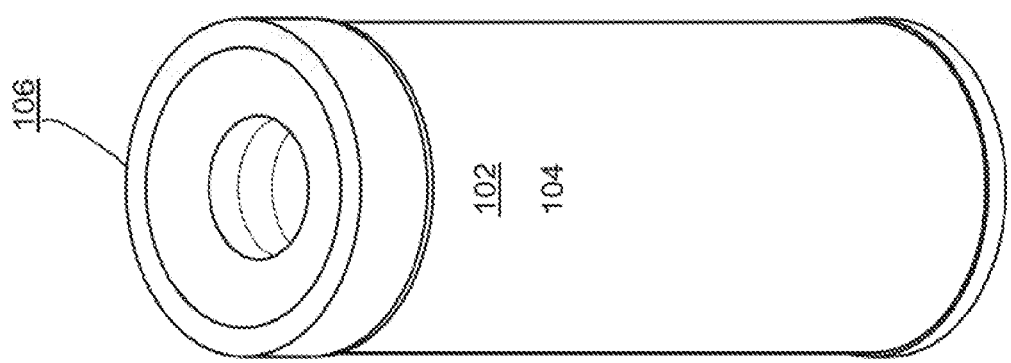

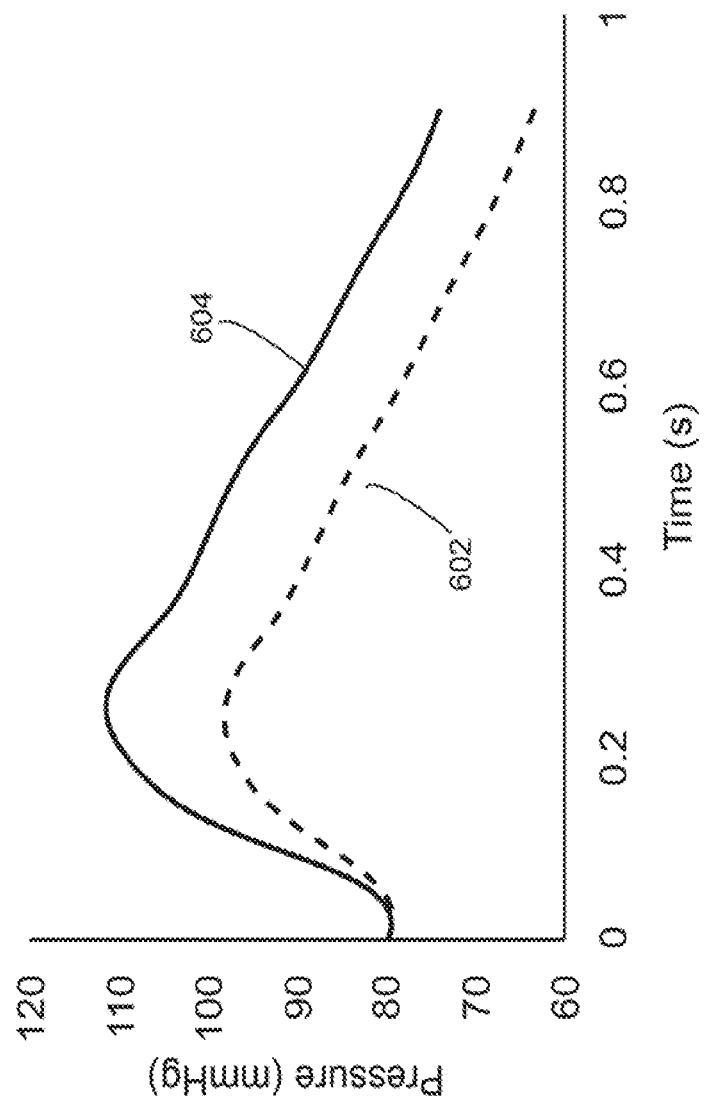

COMPLIANT AORTIC STENT GRAFTS AND RELATED SYSTEMS AND METHODS

PRIORITY CLAIM

The present application is a National Phase entry of PCT Application No. PCT/US2018/029820, filed Apr. 27, 2018, which claims priority from U.S. Provisional Application No. 62/491,546, filed Apr. 28, 2017, each of which is hereby fully incorporated herein by reference.

TECHNICAL FIELD

Embodiments of the present disclosure relate generally to vascular implants, and in particular to vascular implants for deployment in an aorta of a patient.

BACKGROUND

Aortic dissection affects thousands of new patients each year in the United States alone. This acute injury to the aorta is associated with significant morbidity and mortality. The underlying causative factors can include an aortic wall tear that is secondary to hypertension in the setting of a brittle aorta. Surgery is not always recommended for these patients, unless the ascending aorta is involved or the injury is associated with rupture or compromised flow to major organs or tissues. Whether or not surgery is indicated, the remaining aorta is generally managed with aggressive anti-hypertensive therapy in attempts to limit the pressure difference between systole and diastole, and thereby prevent future tears and/or propagation of the existing tear. Good blood pressure management for these patients has proven to be quite challenging, however. Even with anti-hypertensive therapy, survivors of acute aortic dissection have a 20% chance of aortic-related mortality within five years.

A recent development has been the availability of aortic stent grafts, or covered stents. While stent grafts were initially designed for treatment of aortic aneurysms, they also have been used to cover the site of a tear in an aortic dissection. Randomized studies have shown that, in conjunction with ongoing aggressive anti-hypertensive therapy, stent grafting can result in healing of the area of the aorta protected by the endoluminal stent graft (or "endograft"), or covering portion of the stent.

These endovascular procedures are favorable for treatment of cardiovascular disease because they are minimally invasive, but a substantial risk is often overlooked when it comes to thoracic endovascular aortic repair (TEVAR). The aorta is the largest artery in the human body, and it is the main conduit for delivering oxygenated blood to most organs and peripheral vessels. However, in addition to providing a low-resistance route for blood, the aorta is responsible for regulating downstream flow rate. Its elastic nature allows it to expand to accommodate the bolus of blood leaving the heart's left ventricle during cardiac systole and then contract to push that blood along during diastole. This capacitive function is inhibited when the aorta wall stiffens, either naturally with age or due to placement of a rigid stent graft during TEVAR.

Aortic stiffening on its own is a predictor of cardiovascular disease risk in addition to its contribution to increased blood pressure. It is troubling that TEVAR, while treating cardiovascular disease, is also augmenting one of the most significant cardiovascular disease risk factors.

Aortic dissection is one of the main aortic diseases for which TEVAR is employed. Dissection occurs when the aorta wall tears, often forming a false lumen within layers of the wall. This condition can cause poor perfusion to vital organs and risk of fatal rupture of the aorta. Dissections that occur in the descending thoracic aorta are commonly treated with TEVAR to reinforce the torn wall and maintain vessel patency.

Unfortunately, however, neither anti-hypertensive therapy nor segmental coverage of dissected aorta with known rigid stent grafts can reverse the underlying pathology of the aortic wall that lead to the injury. This is because the aorta in the patient with aortic dissection has become rigid and lost much of its original elasticity. This elasticity—a key property of the thoracic aorta imparted by its high elastin content—normally allows for absorption and redistribution of the pressure wave associated with cardiac systole. In other words, the healthy aorta can act as a capacitor with respect to the energy imparted to blood flow during systole. The accommodation of a healthy blood vessel in response to the pulsatile ejection of blood by the heart is depicted in FIG. 1A. During each phase of a heartbeat, the contractions of the chambers of the heart cause a pulse-wave of blood to travel out from the heart through (during systole), or towards the heart (during diastole). A healthy blood vessel is compliant, and able to elastically expand and contract in cross-section in order to accommodate the pressure wave. The flow of blood (and therefore the intraluminary pressure) is therefore relatively stable along the length of the vessel.

Existing aortic endoluminar stent grafts, while FDA approved for treatment of acute aortic dissection, were actually designed for treatment of aortic aneurysms. These metal stent reinforced tubes have some flexibility along their length to accommodate curvature of the aorta, but they are rigid with respect to diameter: they press outward firmly against the inner surface of the aortic wall and do not allow for expansion, either circumferentially or longitudinally, with systole. In theory, the longer the segment of aortic stent graft, the greater the energy that will need to be accommodated by the native aorta on either side of it to dissipate the pressure wave of systole. The effect of this can be seen in FIG. 1B, where rigidity, caused by placement of a conventional stent 10 (or simply due to lost elasticity), can cause perturbations in the blood flow, increasing pulse wave reflections, creating areas of stress 11 both proximal and distal to the rigid span.

This means that while existing grafts may protect the acutely injured aorta, they may actually be deleterious for the remaining native aorta, making this tissue and therefore the patient even more reliant on aggressive blood pressure management. Clinically, this can present as Stent graft Induced New Entry dissections, or SINE, which are new tears induced in the native aorta in regions adjacent to the stent graft. This complication of stent grafts is seen in 30% of patients for whom grafts are placed for aortic dissection. In addition, retrograde type A dissection has been seen in 4% of such patients. In short, care options for aortic dissection are inadequate because they do not treat the underlying problem.

SUMMARY

Embodiments of the present disclosure include compliant vascular implants, including stent grafts and vessel liners that can mimic the elastic properties of the normal, healthy aorta. These improved implants can decrease pressure-induced stresses on the residual native aorta and reduce the secondary risk of SINE dissections.

Embodiments comprise double-tube stent grafts having at least one outer layer similar to current stent grafts, and a flexible or compliant inner liner. These stent grafts are configured to enable the space between the inner and outer layers to be filled with an appropriate filling material. The filling material creates a volume buffer between the layers, allowing the stent grafts to be compliant to luminal pressure. In operation, as blood courses through the lumen of the inner liner, the flexible walls can deform, more closely mimicking the behavior of a healthy vessel.

Embodiments of the present disclosure include a liner for an endoluminal stent or blood vessel, the stent defining a lumen for the passage of blood through a blood vessel. The liner can comprise a flexible bladder arrangeable within the lumen, which can be fillable with a compressible fluid. The bladder can define an inner lumen for the passage of blood. The bladder and the fluid are conformable in response to a pulsatile pressure wave of the blood in the blood vessel such that the pressure within the blood vessel is reduced.

The bladder can comprise a toroid cuff and the liner further comprises: an elongate elastic tube having an axial length at least equivalent to the axial length of the stent. The liner can further comprise a first ring at a first axial extent and a second ring at a second axial extent. The first ring and the second rings can be radially inextensible.

The bladder further can comprise means for filling the bladder to a desired internal pressure. The means for filling the bladder to a desired internal pressure can be a filling port. The filling port can be self-healing, and/or pierceable by a syringe. The means for filling the bladder to a desired internal pressure can be a compressed gas compartment. The compressible fluid can be selected from the group consisting of: air, carbon dioxide, oxygen, and combinations thereof.

In embodiments, the liner can further comprise a capacitive reservoir arrangeable outside of the blood vessel and in fluid communication with the bladder, such that the fluid can be pushed into the capacitive reservoir from the bladder in response to high pressure within the blood vessel, and released from the capacitive reservoir into the bladder in response to low pressure within the blood vessel. In this case, an incompressible fluid such as sterile saline solution could be used to fill the liner.

In embodiments, the bladder can include one or more radially inward facing projections. The projections can be mutually fluidically connected, or disconnected.

In embodiments, a method of deploying a liner for an endoluminal stent graft arranged within a blood vessel includes guiding the liner into a lumen of the stent graft, withdrawing air from the flexible bladder through a first catheter, pumping a compressible fluid into the flexible bladder through the first catheter or a second catheter, and withdrawing the first catheter or the first catheter and the second catheter.

In embodiments, the method can also include monitoring a pressure within the flexible bladder and ceasing the pumping of the compressible fluid when the pressure reaches a desired level. In embodiments, the method can also include monitoring a volume of compressible fluid pumped into the flexible bladder and ceasing the pumping of the compressible fluid when the volume reaches a desired level.

In embodiments, an endoluminal stent graft for deployment within a blood vessel comprises a radially-inextensible elongate support portion defining an outer lumen, a non-porous elastic liner portion that is arrangeable within the outer lumen and fixable to the stent portion at a first end and a second end. A deformable void is defined by the outer lumen and an outer surface of the liner portion when the stent graft is deployed within the blood vessel. The liner portion can also define an inner lumen for the passage of blood. A filling port can be arranged within the elastic liner portion such that the deformable void can be filled with a compressible fluid. The liner portion and the fluid can be conformable in response to a pulsatile pressure increase of the blood in the blood vessel.

In embodiments, the elastic liner portion can have an axial length that is greater than the axial length of the elongate stent portion. The liner portion can be fixable to the stent portion by wrapping a first end of the liner portion around the outer surface of a first end of the stent portion, and wrapping a second end of the liner portion around the outer surface of a second end of the stent portion.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures.

FIG. 1A is a perspective view depicting blood flow in a healthy blood vessel.

FIG. 1B is a perspective view depicting blood flow in a blood vessel with a rigid portion.

FIG. 2A is a perspective view depicting a stent graft according to an embodiment.

FIG. 2B is a transverse cross-sectional view depicting the stent graft of FIG. 2A.

FIG. 2C is a longitudinal cross-sectional view depicting a stent graft according to an embodiment.

FIG. 7A is a transverse cross-sectional view depicting a bladder according to an embodiment.

FIG. 7B is a longitudinal cross-sectional view depicting a bladder, according to an embodiment.

FIG. 8 is a cross-sectional view of an embodiment of a compliant stent graft deployed within a blood vessel.

FIG. 9A is a photographic view of a prototype of a compliant stent according to an embodiment.

FIG. 9B is a photographic view of a prototype of a compliant stent placed in a model vessel, according to an embodiment.

FIG. 10 is a graph depicting results of modeling fluid flow within a vessel.

Figure 1C:
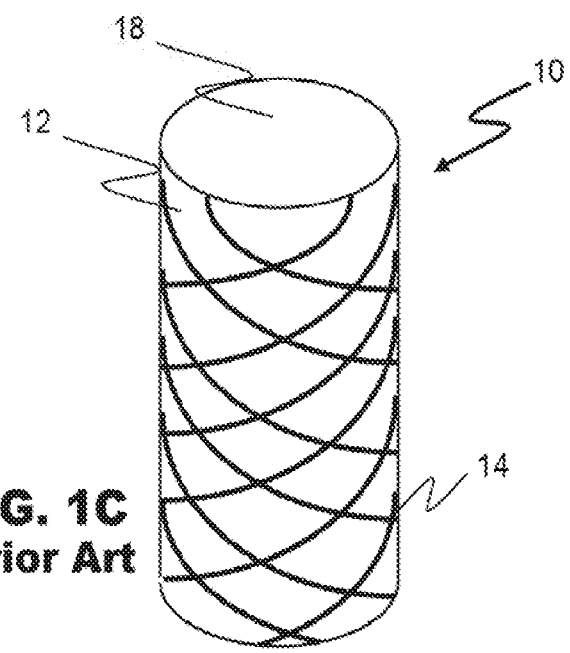
FIG. 1C is a perspective view depicting a conventional stent graft.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Studies have shown that a more compliant aortic model results in significantly reduced systolic blood pressure for a given stroke volume. Embodiments of the present disclosure include compliant stent grafts and vessel liners that can mimic the elastic properties of normal healthy aorta. These improved vascular implants can decrease pressure-induced stresses on the residual native aorta and reduce the secondary risk of SINE dissections. As used herein, "elastic" can refer to an ability expand (stretch) or contract, whereas "flexible" can refer to an ability to bend, or conform without necessarily changing an interior or exterior volume.

Figure 1D:
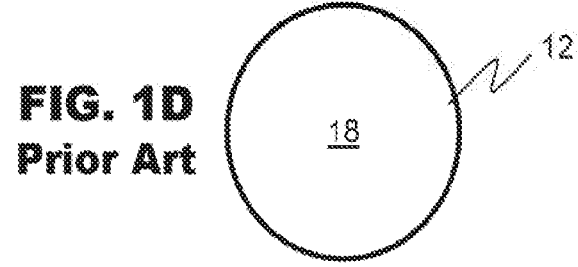
FIG. 1D is a transverse cross-sectional view depicting the conventional stent graft of FIG. 1C.

FIGS. 1C and 1D are perspective and transverse cross-sectional views, respectively, of a conventional stent graft 10. An outer layer 12 surrounds, or is surrounded by, a support layer 14, such as a stent, which defines a lumen 18. In use, stent graft 10 can be deployed to a vessel for treatment along a guidewire catheter or other method known in the art. While conventional stent grafts provide flexibility along their length in order to be navigated through vessels, once deployed, outer layer 12 is radially inextensible, and therefore stent graft 10 is not compliant in diameter or length, so acts as a rigid tube within the vessel.

FIGS. 2A and 2B are perspective and transverse cross-sectional views, respectively, of an improved stent graft 100, according to an embodiment of the present disclosure. Stent graft 100 can include outer layer 102, support layer 104, and flexible inner liner 106 which defines lumen 108. Either one or both of outer layer 102 or support layer 104 can be rigid (i.e. radially inextensible).

In embodiments, outer layer 102 can comprise polyester, polytetrafluoroethylene (PTFE), expanded PTFE (ePTFE), or any other non-porous biocompatible material suitable for a stent graft. In embodiments, outer layer 102 can comprise biological materials, such as those disclosed in U.S. Pat. No. 6,926,743 to Chuter, which is incorporated herein by reference to the extent it is consistent with the instant disclosure.

Support layer 104 is configured to provide sufficient support to protect a torn vessel wall. Accordingly, support layer 104 can comprise a solid, porous, braided, or mesh stent, such as those known in the art. Similarly, support layer 104 can comprise memory metals, memory plastics, or any other materials suitable for construction of stents, such as those described in U.S. Pat. No. 8,821,564 to Schreck et al., which is incorporated herein by reference to the extent it is consistent with the instant disclosure. In some embodiments, outer layer 102 can be constructed to provide the necessary support and support layer 104 is omitted.

Inner liner 106 can comprise silicone, polyester, PTFE, ePTFE, or any other flexible, elastic, and nonporous, biocompatible material that can be expanded and contracted radially and axially. Inner liner 106 can be configured so as to define a fillable void 110 between support layer 104 and inner liner 106. Void 110 can be filled with a compressible fluid 112 or other appropriate filling material. In embodiments, compressible fluid 112 is in a gaseous state at the temperatures and pressures present within the body and comprises material that can be readily reabsorbed by the body. Compressible fluid 112 can be or comprise carbon dioxide, air or some other compressible biocompatible material or combination of materials of suitable density and viscosity to allow lumen 108 to deform in a way that mimics the behavior of a healthy vessel in response to blood flow and provide support for the stent. When present, the compressible fluid 112 creates a compliant volume buffer between the layers.

In one embodiment, depicted in FIG. 2C, inner liner 106 can comprise an elastic tube. The ends of inner liner 106 can be wrapped around the outer surface of support layer 104. The ends of inner liner 106 can be fixed to support layer 104 by being sewn in place, fixed with adhesive, fused, or through other means. Air trapped between the elastic tube and the outer wall can be evacuated using a syringe. The syringe can be inserted through a filling port (not shown), or directly through the material of inner liner 106, especially where inner liner 106 comprises a self-healing material.

Stent graft 100 can be primarily tubular, or can be bifurcated. Where stent graft 100 is bifurcated, it can present legs (not shown). Bifurcated stent graft 100 can be constructed in a unitary fashion, or one or both legs can be deployed separately from the main body of stent graft 100.

Figure 3A:
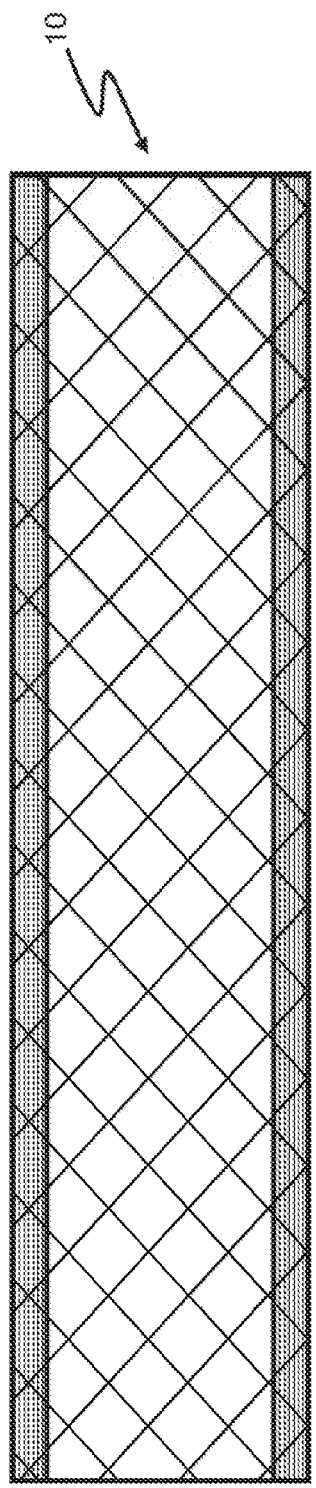
FIG. 3A is a longitudinal cross-sectional view depicting a conventional stent graft.
Figure 3B:
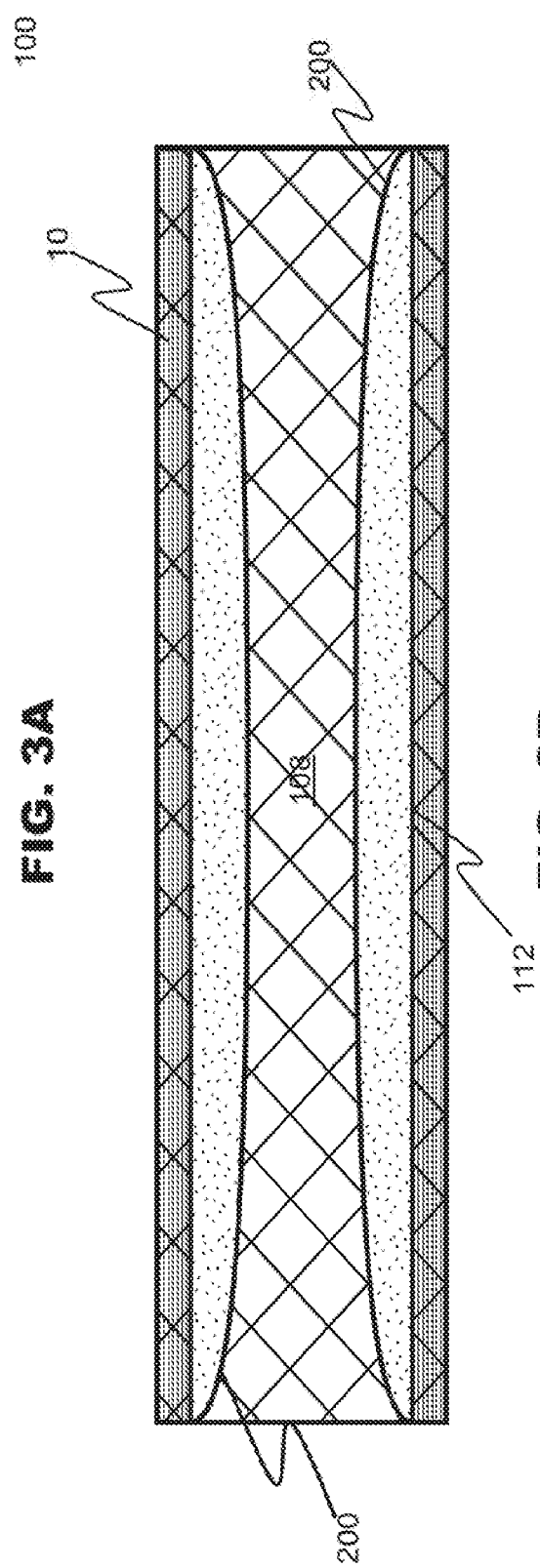
FIG. 3B is a longitudinal cross-sectional view depicting a stent graft according to an embodiment.

While stent graft 100 can maintain a layer of fluid 112 within void 110 between inner liner 106 and outer layer 102, embodiments of the present disclosure include other containment methods. As depicted in FIGS. 3A and 3B, embodiments comprise a liner 200, which can be deployed into an existing stent or stent graft such as conventional endoluminal stent graft 10, enabling the passage of blood through lumen 108. Liner 200 can also be deployed directly into a vessel. Liner 200 can comprise a flexible or elastic bladder 114, for containment of fluid 112.

Figures 4A, 4B:
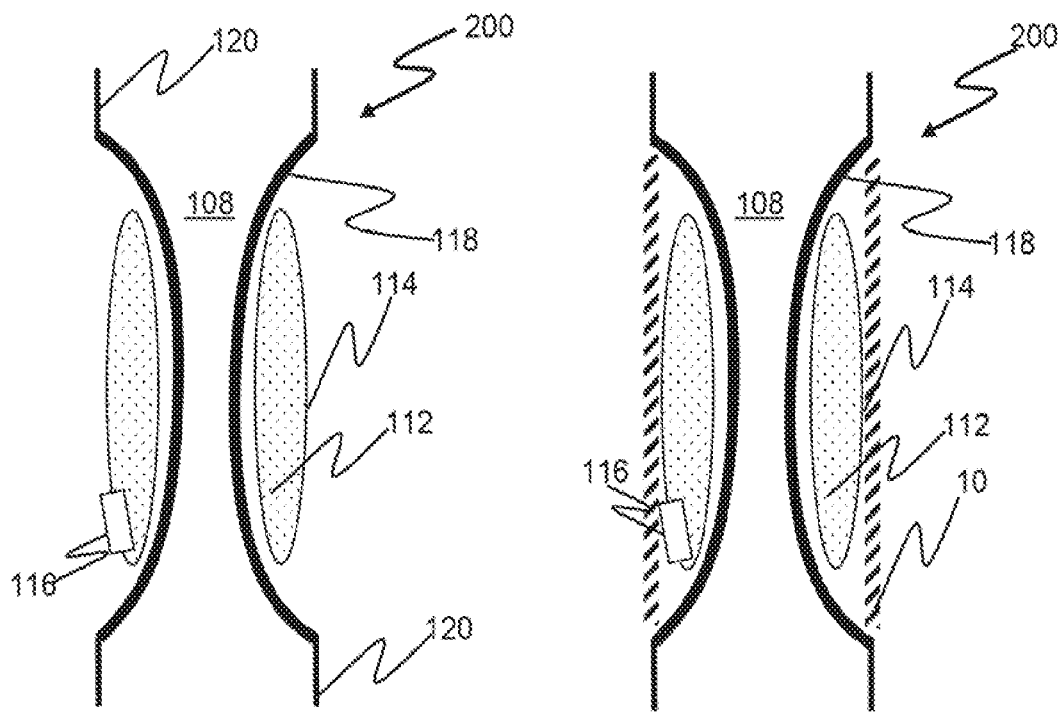
FIG. 4A is a longitudinal cross-sectional view depicting a liner according to an embodiment.
FIG. 4B is a longitudinal cross-sectional view depicting the liner of FIG. 4A deployed within a rigid vascular implant.

FIGS. 4A and 4B are partial cross-sectional views of a liner 200 according to an embodiment. Bladder 114 can comprise a fillable toroid cuff that can be arranged within the lumen of a stent (or stent graft 10). Bladder 114 can further comprise a filling port 116. Filling port 116 can be a one-way membrane, self-healing membrane, aperture, or other passage through which bladder 114 can be evacuated of air or other unwanted material, and filled with compressible fluid 112.

Figures 5A, 5B:
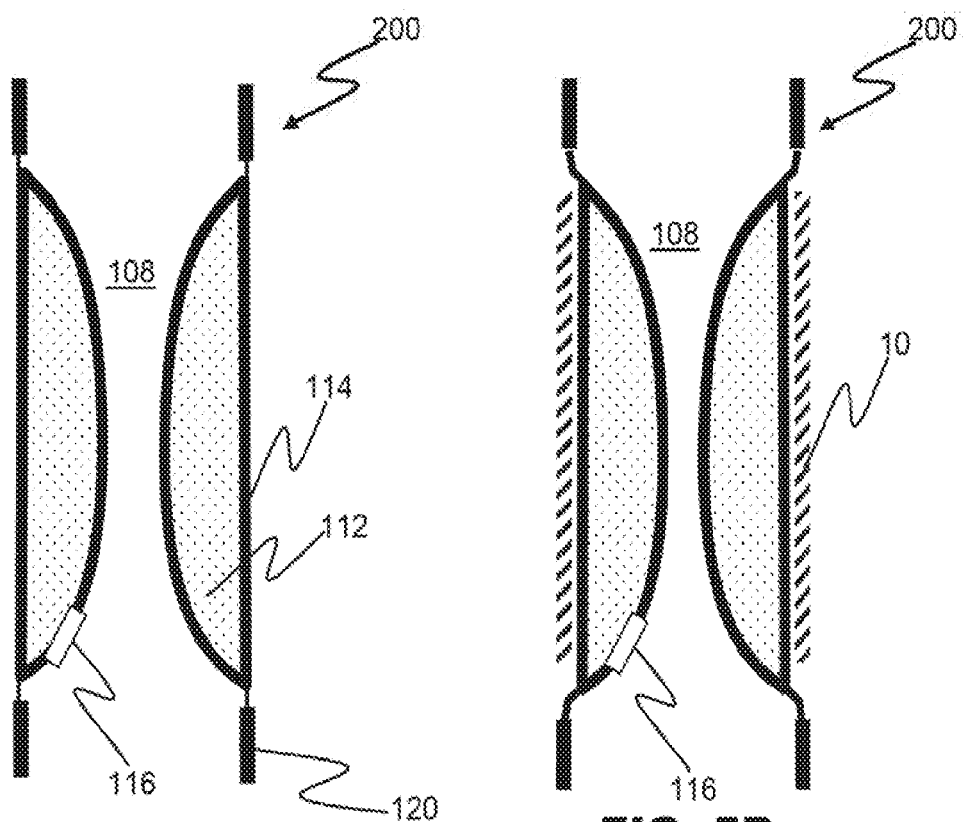
FIG. 5A is a longitudinal cross-sectional view depicting a liner according to an embodiment.
FIG. 5B is a longitudinal cross-sectional view depicting the liner of FIG. 5A deployed within a stent.

As depicted in FIGS. 4A and 4B, bladder 114 can be held within the lumen of stent 10 by an elastic tube 118, which can have rigid (or radially inextensible) ends 120 that extend axially beyond stent 10. Ends 120 can be rings coupled to the axial extents of stent 10 by adhesives, sewn seams (such as sutures) or other means. Lumen 108 can be defined by the inner surface of tube 118. In embodiments, ends 120 can be stitched directly to the tissue of the blood vessel after or during deployment of liner 200. As depicted in FIGS. 5A-5B, in embodiments bladder 114 can be directly fixed to ends 120, such that elastic tube 118 is not necessary. Lumen 108 can therefore be defined by one or more inner surfaces of bladder 114.

Figure 6A:
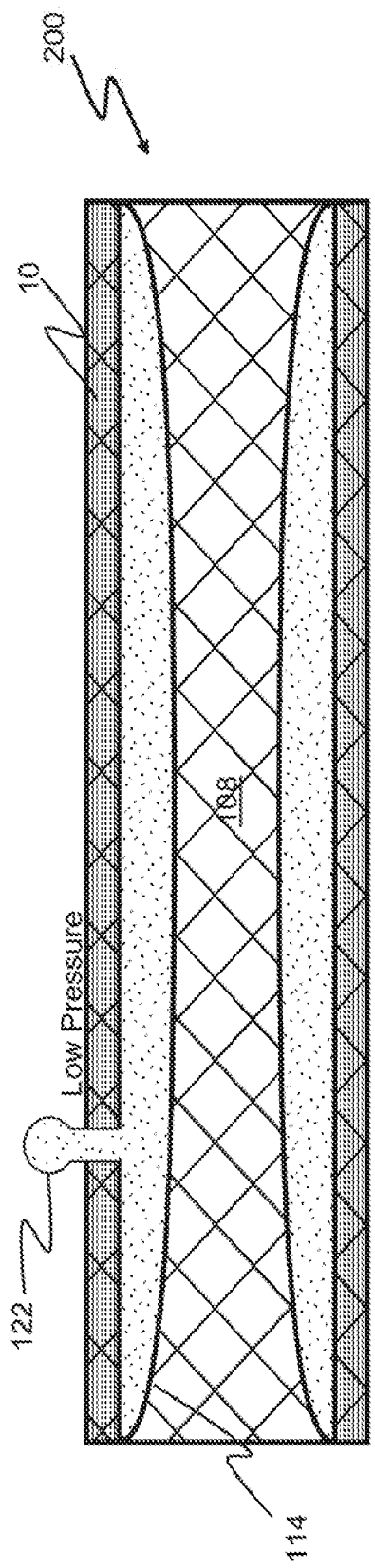
FIG. 6A is a longitudinal cross-sectional view depicting a liner at lower pressures according to an embodiment.
Figure 6B:
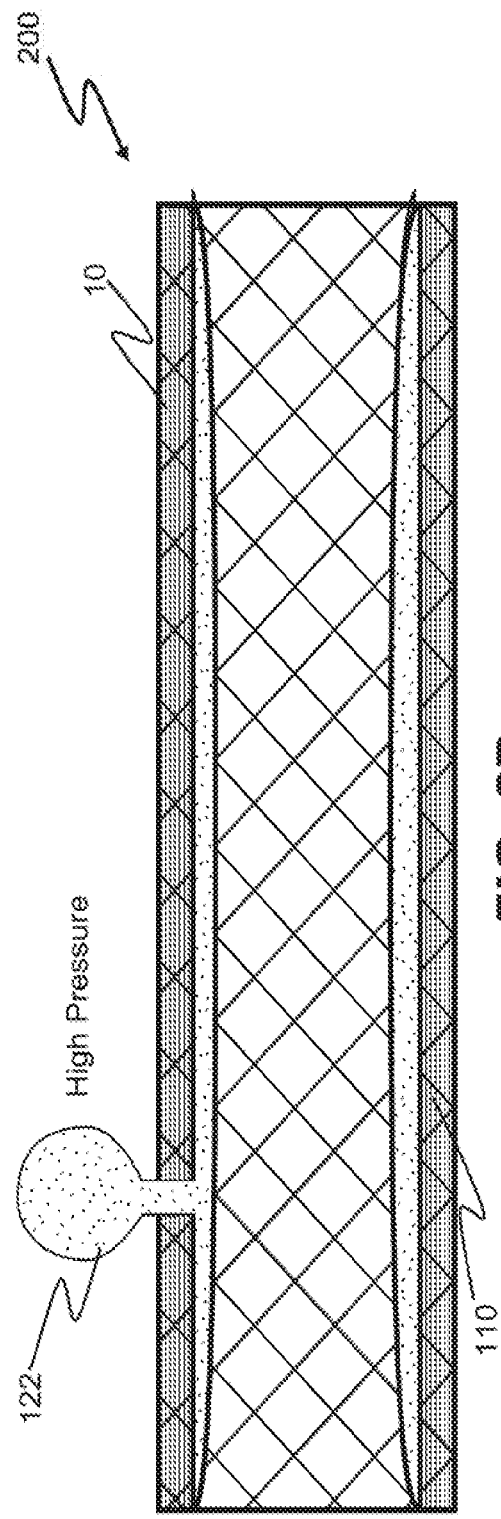
FIG. 6B is a longitudinal cross-sectional view depicting a liner at higher pressures according to an embodiment.

FIGS. 6A and 6B are cross-sectional views depicting an embodiment wherein bladder 114 is in fluid communication with an elastic capacitive reservoir 122. Capacitive reservoir 122 can be arranged outside of stent graft 10 through an aperture in the blood vessel (for example, through the original dissection, or through a surgically created aperture. Capacitive reservoir 122 can expand to receive fluid 112 as pressure increases within lumen 108. Capacitive reservoir 122 can contract to push fluid into bladder 114 as the luminary pressure is reduced. Capacitive reservoir 122 therefore enables bladder 114 to conform based on luminary pressure, even when fluid 112 is a less compressible fluid (such as a sterile saline solution or other liquids).

While generally depicted as a toroid herein, bladder 114 can have other forms. For example, bladder 114 can comprise one or more discrete fillable portions arranged about the inner surface of liner 200. In embodiments, the fillable portions can be interconnected such that fluid 112 can pass between portions in response to the pressure in the vessel. FIG. 7A is a cross-sectional view depicting bladder 114 comprising a plurality of elongate channels 124. Channels 124 can extend along the entire length of liner 200, or portions thereof. Channels 124 can be fluidly connected as depicted, or separate. FIG. 7B is a plan view depicting bladder 114 with a plurality of partially elongate, discrete channels 124.

Each of bladder 114 and liner 200 can have an elongate length equal to, greater than, or less than an existing stent graft 10. Bladder 114 can have an elongate length less than liner 200. Bladder 114 and liner 200 can therefore be used with stent grafts have a variety of lengths.

In operation, as blood flows through the lumen 108, the conformable inner surfaces of embodiments of the present disclosure can deform to more closely mimic the behavior of a healthy vessel. FIG. 8 is a cross-sectional view of a vascular implant according to an embodiment (such as stent graft 100 or liner 200) fully deployed within a vessel. As the pulse-wave travels along the vessel, lumen 108 is deformed in compliance with the luminary pressure, which inhibits vorticity and pulse wave reflections at the areas of stress 11.

In use, stent graft 100 and/or liner 200 can be deployed on a guidewire, balloon guidewire, or other deployment system known in the art or customized for use with stent graft 100. After deployment, the guidewire can be retracted, and compressible fluid 112 can be injected into void 110 or bladder 114. Alternatively, compressible fluid 112 can be injected prior to deployment. Liner 200 can be deployed into the lumen of an existing stent or stent graft, or directly into a vessel.

Compressible fluid 112 can be injected into void 110 or bladder 114 via filling port 116 or directly through the material of bladder 114 or inner liner 106. Compressible fluid 112 can be inserted via a syringe and/or catheter. In yet other embodiments, compressible fluid 112 can be provided within bladder 114 before deployment, and released via a charge (such as compressed carbon dioxide, or a chemically activatable charge) to inflate bladder 114 as needed.

Figure 9C:
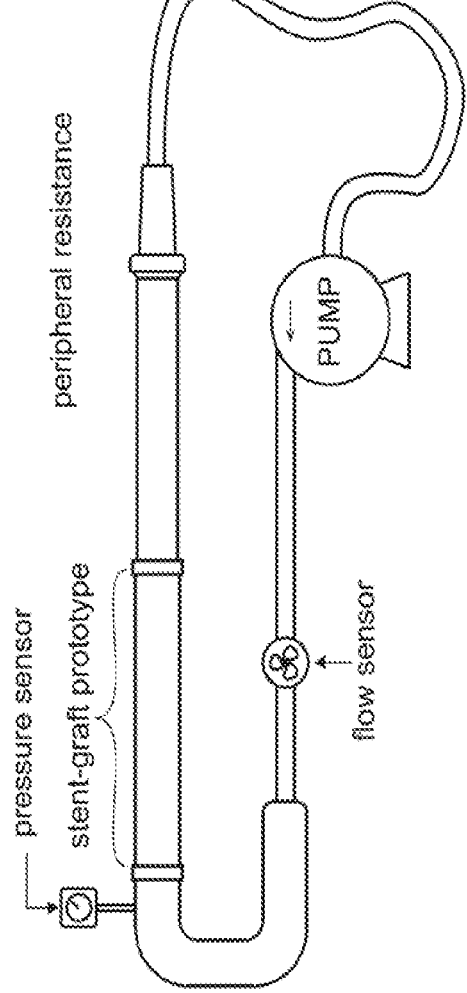
FIG. 9C is a schematic view of a testing system for a vascular implant according to an embodiment.
Figure 9D:
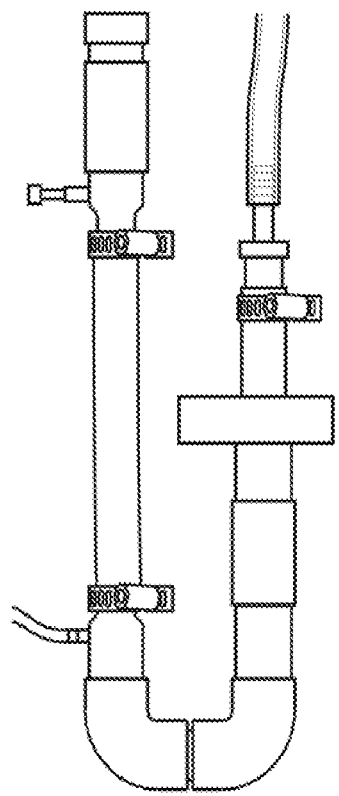
FIG. 9D is a photographic view of testing system for a vascular implant according to an embodiment.

FIGS. 9A and 9B are photographic views of a macro-scale prototype of an embodiment of a stent graft. FIG. 9A depicts the prototype independently. FIG. 9B depicts the prototype as mounted in a PVC model of the aorta. Outer layer 102 and support layer 104 are represented here by white PVC pipe. Inner liner 106 is represented by an elastomer material. While the prototype may be unsuitable for clinical deployment in human patients, it is magnetic resonance imaging compatible and can be used for flow studies. FIGS. 9C and 9D are schematic and photographic views of a test apparatus that can be used to model the response of compliant vascular implants within a vessel.

Figure 11:
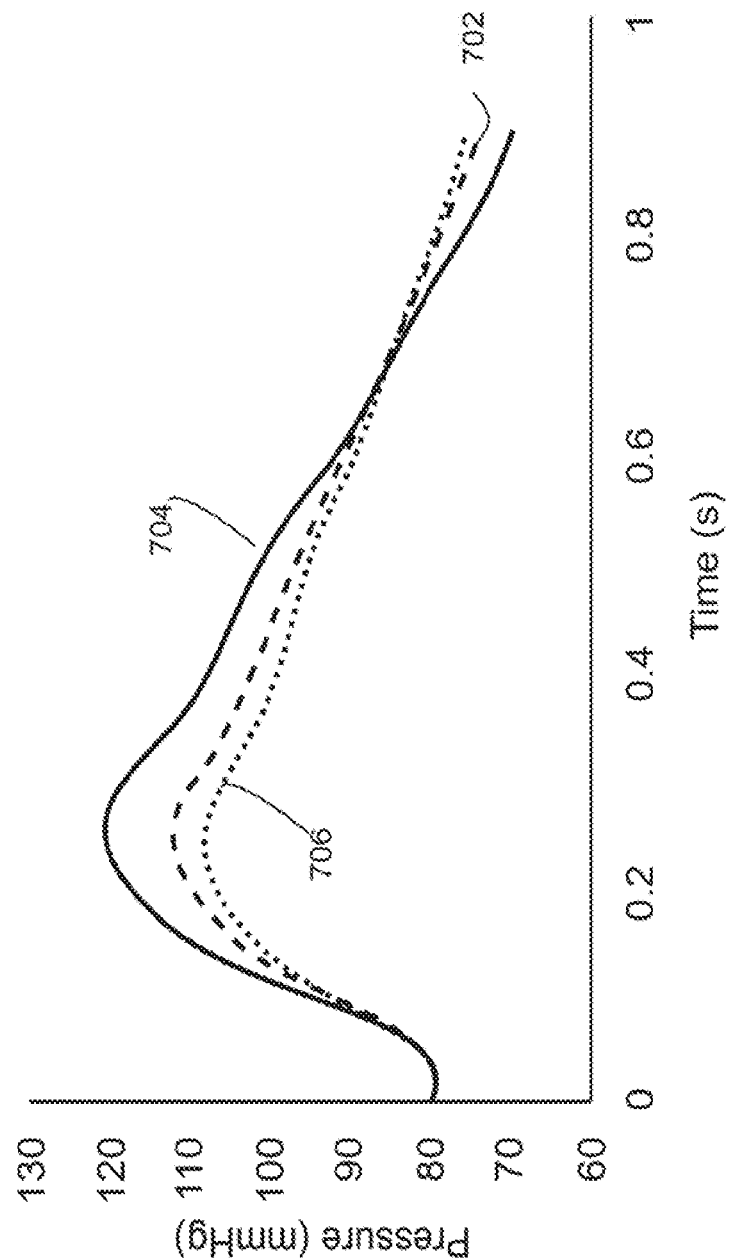
FIG. 11 is a graph depicting results of modeling fluid flow within a vessel.

When modeled, a standard stent graft displays attributes similar to models of a rigid tube. FIGS. 10 and 11 represent the results of lumped parameter mathematical modeling of flow through the descending thoracic aorta. FIG. 10 is a graph depicting an increase in peak pressure for patients with a rigid stent graft. The graph of FIG. 10 depicts the proximal native aorta pressure predicted using the lumped parameter model. Curve 602 (dashed) represents the predicted pressure for a patient without a stent graft, and curve 604 (solid) represents the predicted pressure with a standard stent graft.

The length of the stent graft also has an effect when modeled. FIG. 11 is a graph depicting the effect of stent graft length on proximal native aorta pressure. Curve 702 (dashed) represents the pressure over time in a patient with a rigid stent graft. Curve 704 (solid) represents a patient with a longer rigid stent graft (than that of curve 702). Curve 706 (dotted) represents a patient with a shorter rigid stent graft (than that of curve 702).

Figure 12:
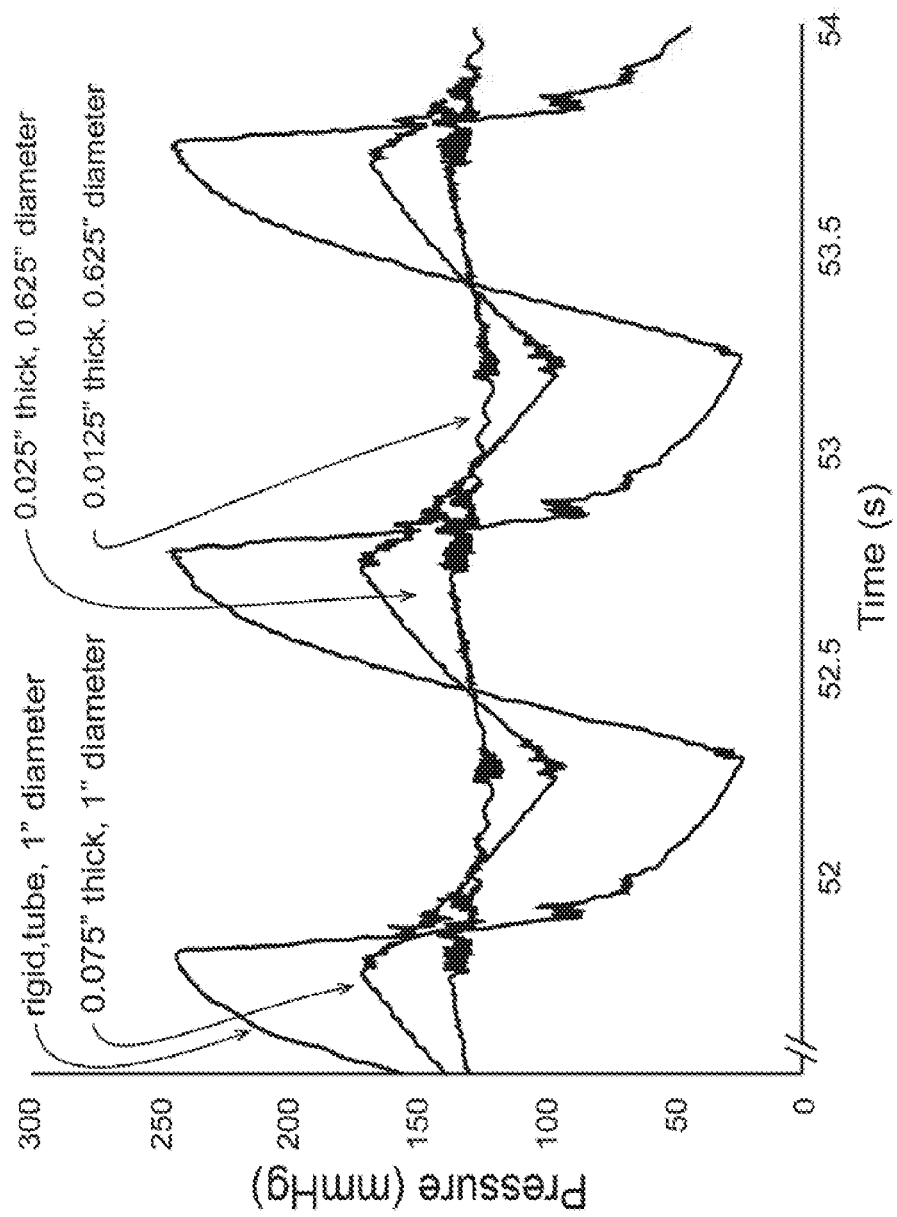
FIG. 12 is a graph depicting results of modeling fluid flow within a vessel.

The system of FIGS. 9C and 9D can be used to model the pressure versus time for various diameters and thicknesses (indicative of compliancy) of tubes. Rigid piping with one-inch inner diameter can be used to represent most of the aorta. In the descending aorta, latex tubes of various thicknesses can be placed in a series of tests to achieve different levels of increased compliance in that section. A downstream restrictor can simulate resistance of the peripheral vessels. A pulsatile flow rate can be imposed by the pump, and a sensor upstream of the test section can record pressure. A water-glycerol solution can be used to match blood viscosity. The results of such testing can be seen in FIG. 12.

Figure 13:
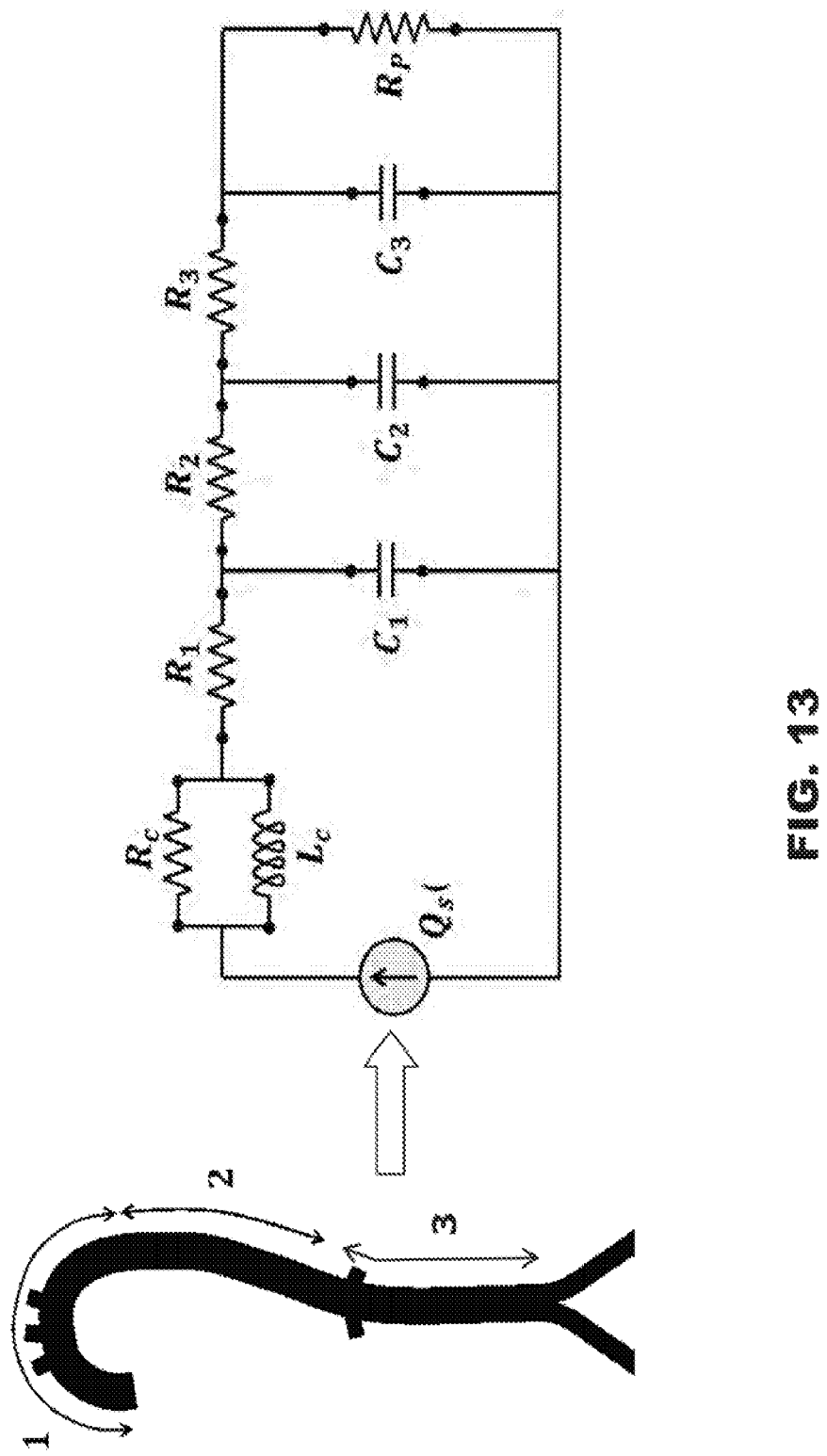
FIG. 13 is a schematic view depicting an electrical circuit model of fluid flow within a vessel.
Figure 14:
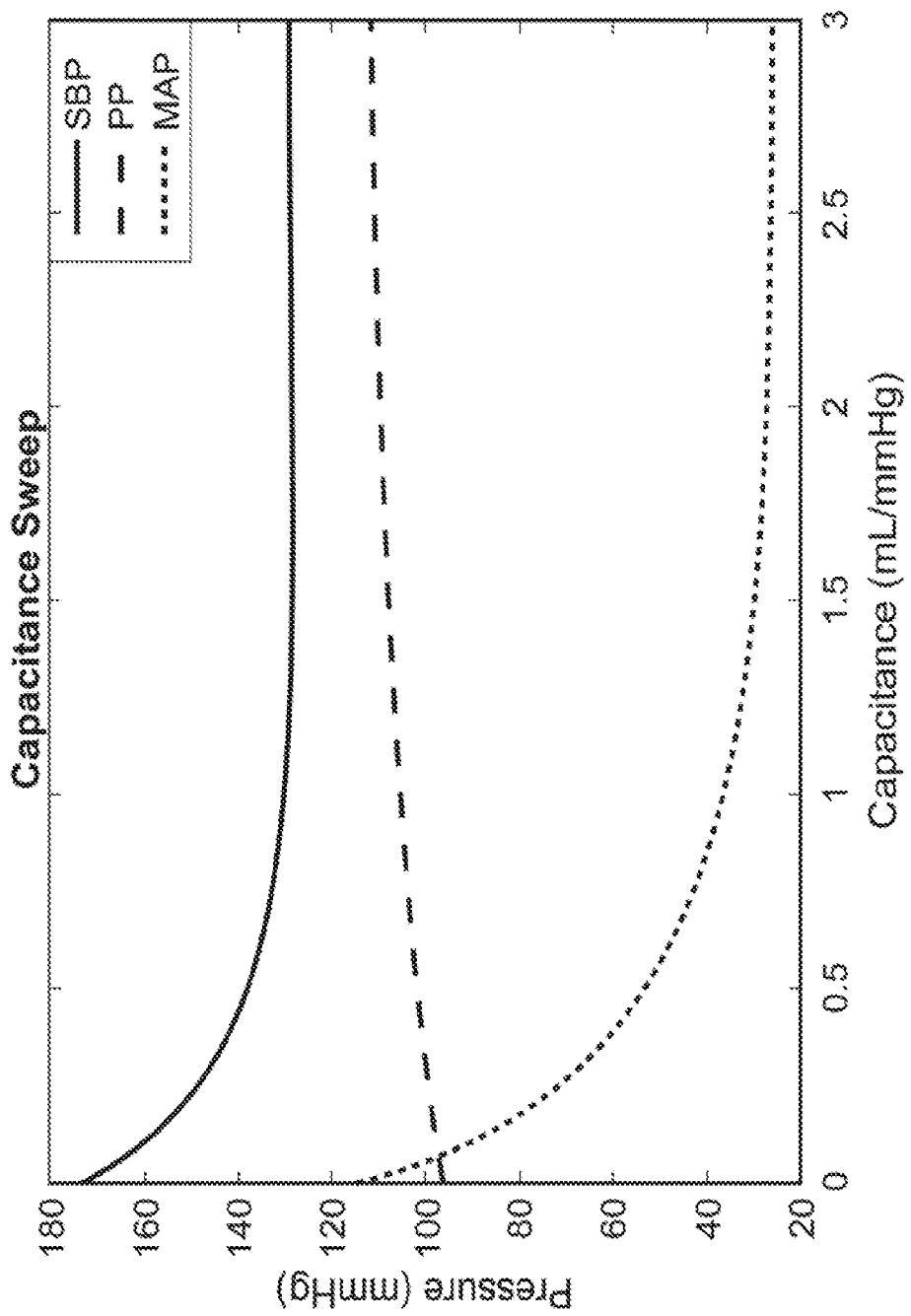
FIG. 14 is a graph depicting results of modeling fluid flow within a vessel.

The lumped parameter model can be built upon the four-element Windkessel model, to simulate an arterial system with a stent graft based on models of electrical circuits, as depicted in FIG. 13. Three capacitor-resistor sets can represent the ascending 1, descending 2, and abdominal 3 aortic segments of a patient. Capacitance C and resistance R for the aortic segments can be calculated using equations for flow through an elastic tube:

$$C = KV = \frac{r}{t} \cdot \frac{\pi r^2 L}{E}, \quad R = \frac{8\eta L}{\pi r^4}$$

Where the values for length, L, radius r, thickness t, and elasticity E of the vessels can be constants based on empirical data. The viscosity of the blood, $\eta$, can be held constant. The stiffness constant K for capacitance can be obtained using Laplace's Law. Parameters $R_c$ and $L_c$ represent the characteristic impedance of the heart outlet and entrance to the most proximal ascending aorta. $R_P$ is the lumped resistance of the peripheral vasculature.

Where $R_2$ is held constant, and $C_2$ (the capacitance of a stent-graft or liner within the descending aorta) incremented, the resulting pressure trend can be observed, for example as depicted in FIG. 14. Systolic blood pressure (SBP) is the peak output pressure, while mean arterial pressure (MAP) and pulse pressure (PP) are given by:

PP=SBP−DBP

MAP=⅓SBP+⅔DBP where diastolic (DBP) is the minimum pressure. As can be seen in FIG. 14, SBP shows a non-monotonic relationship with stent graft capacitance, while PP and MAP have opposite reactions to increasing capacitance.

The modeled results of FIGS. 10 and 11 show that rigid stent grafts may themselves exacerbate pressure on the residual aorta. These regions of native aorta proximal to the stent graft are required to limit pressure differences, inducing larger stresses and increasing the potential of aortic tearing.

Similar modeling shows that by increasing the compliance of the tube, significant reductions in peak systolic pressure can be effected. This reduction in pressure can provide better protection for existing tears and reduce the risk of SINE dissections. Embodiments of the present disclosure, therefore, include a flexible, compliant inner liner, which is separated from the rigid outer layer by a filling material within the intervening void space. The filling material is provided at a pressure enabling the inner liner to deform to accommodate the pulse wave of a heartbeat in order to better mimic the compliance of a healthy vessel.

Embodiments of the present disclosure can be used to preserve, or even reduce, blood pressure, even in patients who have not experienced aortic dissection or tears.

While embodiments of the present disclosure have been discussed herein in reference to deployment within an aorta, those of ordinary skill in the art will appreciate that the embodiments disclosed can be adapted for other clinical uses, such as deployment within other blood vessels, or other vessels such as those of the gastroenterological system (for example, the intestines).

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A liner for a vascular implant, the vascular implant defining a lumen for the passage of blood through a blood vessel, the liner comprising:
   a flexible bladder arrangeable within the lumen and fillable with a compressible fluid, the bladder defining an inner lumen for the passage of blood; and
   a plurality of discrete fillable portions extending primarily along a length of the inner lumen, the plurality of discrete fillable portions fluidly interconnected with one another;
   wherein the bladder and the fluid are conformable in response to a pulsatile pressure wave of the blood in the blood vessel such that the lumen can continually deform to mimic a healthy vessel such that the pressure within the blood vessel is reduced.

2. The liner of claim 1 wherein the bladder comprises a toroid cuff and the liner further comprises: an elongate elastic tube having an axial length at least equivalent to the axial length of the vascular implant.

3. The liner of claim 2, wherein the liner further comprises a first ring at a first axial extent and a second ring at a second axial extent, the first ring and the second ring being radially inextensible.

4. The liner of claim 1, wherein the bladder further comprises means for filling the bladder to a desired internal pressure.

5. The liner of claim 4, wherein the means for filling the bladder to a desired internal pressure comprise a self-healing, syringe-accessible filling port.

6. The liner of claim 4, wherein the means for filling the bladder to a desired internal pressure comprise a compressed gas compartment.

7. The liner of claim 1, wherein the compressible fluid is selected from the group consisting of: air, carbon dioxide, oxygen, and combinations thereof.

8. The liner of claim 1, further comprising a capacitive reservoir arrangeable outside of the blood vessel and in fluid communication with the bladder, such that the fluid can be pushed into the capacitive reservoir from the bladder in response to high pressure within the blood vessel, and released from the capacitive reservoir into the bladder in response to low pressure within the blood vessel.

9. The liner of claim 1, wherein the bladder comprises one or more radially inward facing projections.

10. The liner of claim 9, comprising a plurality of mutually fluidically-connected projections.

11. The liner of claim 9, comprising a least two projections that are not fluidically-connected.

12. The liner of claim 1 wherein the flexible bladder is constructed of an elastic material.

13. The liner of claim 1 wherein the flexible bladder is fixable to the vascular implant at a first end and a second end of the vascular implant.

14. The liner of claim 1 wherein a deformable void is defined between the lumen of the vascular implant and the flexible bladder.

15. The liner of claim 1 wherein the elastic liner portion has an axial length that is greater than the axial length of the vascular implant, wherein the flexible bladder is fixable to the vascular implant by wrapping a first end of the flexible bladder around an outer surface of a first end of the vascular implant, and wrapping a second end of the flexible bladder around the outer surface of a second end of the vascular implant.

16. A liner for a radially-inextensible lumen within a blood vessel, the liner comprising:

a flexible bladder arrangeable within the radially-inextensible lumen and fillable with a compressible fluid, the bladder defining an inner lumen for the passage of blood; and a plurality of discrete fillable portions extending primarily along a length of the radially-inextensible lumen, the plurality of discrete fillable portions fluidly interconnected with one another;

wherein the bladder and the fluid are conformable in response to a pulsatile pressure wave of the blood in the blood vessel such that the lumen can continually deform to mimic a healthy vessel such that the pressure within the blood vessel is reduced.

17. The liner of claim 16, wherein the radially-inextensible lumen is defined by a vascular implant.

18. The liner of claim 17, wherein the radially-inextensible lumen is defined by an outer boundary which coincides with the inner surfaces of the blood vessel.

* * * * *